(12) United States Patent  
Torales

(10) Patent No.: US 10,792,144 B2
(45) Date of Patent: Oct. 6, 2020

(54) LONGITUDINALLY AND RADIALLY FLEXIBLE ANASTOMOSIS STENT

(71) Applicant: Nelson Rene Torales, Formosa (AR)

(72) Inventor: Nelson Rene Torales, Formosa (AR)

(*) Notice: Subject to any disclaimer, the term of this patent is extended or adjusted under 35 U.S.C. 154(b) by 280 days.

(21) Appl. No.: 15/805,243

(22) Filed: Nov. 7, 2017

(65) Prior Publication Data

US 2019/0133748 A1   May 9, 2019

(51) Int. Cl.
A61F 2/06      (2013.01)
A61F 2/915    (2013.01)
A61B 17/11    (2006.01)

(52) U.S. Cl.
CPC .............. *A61F 2/064* (2013.01); *A61B 17/11* (2013.01); *A61F 2/915* (2013.01); *A61F 2002/91541* (2013.01); *A61F 2002/91575* (2013.01); *A61F 2210/0014* (2013.01); *A61F 2210/0076* (2013.01); *A61F 2250/0039* (2013.01); *A61F 2250/0097* (2013.01); *A61F 2250/0098* (2013.01)

(58) Field of Classification Search
CPC .. A61F 2/064; A61F 2/915; A61F 2002/9155; A61F 2002/91541; A61F 2002/91575; A61B 17/11
See application file for complete search history.

(56) References Cited

U.S. PATENT DOCUMENTS

| | | | |
|---|---|---|---|
| 6,245,100 B1 | 6/2001 | Davila et al. | |
| 6,245,103 B1 | 6/2001 | Stinson | |
| 7,018,401 B1 | 3/2006 | Hyodoh et al. | |
| 7,918,880 B2 | 4/2011 | Austin | |
| 8,419,786 B2 | 4/2013 | Cottone, Jr. et al. | |
| 8,936,827 B2 | 1/2015 | Pacetti | |
| 8,998,975 B2 | 4/2015 | Rowe | |
| 2003/0204244 A1* | 10/2003 | Stiger | A61F 2/90 623/1.16 |
| 2004/0088007 A1 | 5/2004 | Eidenschink | |
| 2014/0058455 A1* | 2/2014 | Appenzeller | A61B 17/8057 606/281 |
| 2014/0207227 A1 | 7/2014 | McGhie | |
| 2016/0143755 A1 | 5/2016 | Nishigishi | |

* cited by examiner

Primary Examiner — Ashley L Fishback
(74) Attorney, Agent, or Firm — Glenn E. Gold, P.A.; Glenn E. Gold

(57) ABSTRACT

An anastomosis stent includes an elongated body of a tubular configuration having a length and diameter dimensions extending in axial and radial directions of the elongated body and in a transverse relationship to each other. The elongated body is formed by multiple rings stacked adjacent one another in a direction parallel to the length dimension. Each ring is a single strand of wire bent in a repetitive pattern of sine waves. Each sine wave defines an alternating peak and valley divided by a length dimension extending orthogonal to the length dimension of the elongated body. The rings are fused together at locations on selected pairs of adjacent peaks and valleys of the rings with the fused locations arranged in parallel rows. The elongated body includes main and end portion and a safety mark about the elongated body at the juncture therebetween.

11 Claims, 10 Drawing Sheets

LONGITUDINALLY AND RADIALLY FLEXIBLE ANASTOMOSIS STENT

FIELD OF THE INVENTION

The present invention generally relates to a surgical anastomosis arterial bypass procedure and, more particularly, is concerned with a longitudinally and radially flexible anastomosis stent.

BACKGROUND OF THE INVENTION

Coronary artery disease, commonly known as CAD, is the most common form of heart disease and is the leading cause of death in the United States for both men and woman. CAD occurs when the arteries that supply blood to the heart muscle become hardened and narrowed. The hardening and narrowing of the blood vessel typical occur due to the buildup in cholesterol (i.e. a waxy, fat-like substance that occurs naturally in the body), and other substances, referred to as plaque, on the arteries' interior wall. The build-up of plaque is commonly referred to as atherosclerosis. As the atherosclerosis occurs (i.e. plaque build-up), less blood is able to flow through the arteries. As a result, the heart muscle isn't able to get enough blood or oxygen needed for it to properly function. The lack of blood and oxygen generally leads to chest pain, referred to as angina, or in worst cases a heart attack. A heart attack typically occurs when a blood clot is so large that it cuts off the blood supply to the heart, causing permanent heart damage.

To combat heart disease many doctors turn to dietary restrictions and prescribe supervised physical activities. However, for some patients a life style change in their diet and activity regime isn't enough to reverse the effects of CAD. Therefore, doctors and surgeons alike have turned to alternative surgical methods to overcome the diminishment of blood and oxygen being supplied to the heart because of atherosclerosis.

One solution that has proven to be successful is coronary artery bypass surgery. The general summary of the procedure includes creating a new path for blood to flow into the heart. This is carried out by a surgeon taking a healthy piece of vein from the leg or artery from the chest or wrist. The surgeon then attaches the dissected portion of the vein and attaches it to the coronary artery, just above and below the narrowed area or blockage. This allows blood to bypass (i.e. get around) the blockage and restore a good blood flow and oxygen flow to the heart. In some instances, multiple bypasses are needed to restore the appropriate amount of blood flow to the heart to stabilize the patient.

Although bypass surgery is a viable option to restore positive blood and oxygen flow to the heart, it may not be the best suitable option for patients who are healthy enough to seek alternative doctor-recommended procedures. For example, the insertion of a balloon angioplasty. Angioplasty and coronary stent placement is the insertion of a stent inside of the coronary artery to help keep the artery way open. To place the stent, a small incision can be made in the groin area to reach an artery, such as the femoral artery. A catheter is then guided through the artery into an area of where the coronary artery is blocked. Once reached, the stent along with a balloon catheter is introduced and expanded, expanding the stent radially outward towards the interior walls of the artery. The stent is then left in the artery to help keep the artery open so that a healthy supply of blood may flow to the heart.

However, both options have their disadvantages and risk. For instance, as with any open-heart surgery, heart bypass surgery carries the risk of complications due to infection, blood clots, heart attack, and stroke to name a few. Likewise, angioplasty risks include, but are not limited to, re-narrowing of the artery (i.e. restenosis), blood clots, and bleeding. Further still, neither of these options may be available to a number of patients because of their current health status and/or medical history.

Therefore, there is a long-felt but, as-of-yet, unmet need in the art for an innovation that will overcome any deficiency and risk of past approaches and any problems that may still be unsolved.

SUMMARY OF THE INVENTION

The present invention is directed to an innovation providing a longitudinally and radially flexible anastomosis stent that overcomes the deficiencies of the known art and the problems that remain unsolved.

In one aspect of the present invention, an anastomosis stent includes:
 an elongated body of a tubular configuration and having a length dimension extending in an axial (longitudinal) direction of the elongated body and a diameter dimension extending in a radial direction of the elongated body being in a transverse relationship to the axial direction of the elongated body;
 the elongated body being formed by a multiplicity of rings stacked adjacent to one another in a direction parallel to the length dimension of the elongated body, each of the rings being formed by a single strand of wire bent in a repetitive pattern of sine waves;
 each of the sine waves defining an alternating peak and valley divided by a length dimension extending orthogonal to the length dimension of the elongated body; and
 the multiplicity of rings being fused to one another at locations on selected pairs of adjacent peaks and valleys of the rings so as to provide flexibility of the rings in the radial direction relative to the axial direction of the elongated body.

In another aspect of the present invention, the single wire of each of the rings is made of a nitinol alloy.

In another aspect of the present invention, the alternating peaks and valleys of the repetitive sine waves of the single strand of wire of a given ring are reversed in adjacent ones of the rings extending along opposite upper and lower sides of the given ring. The fused locations on selected pairs of adjacent peaks and valleys of the rings are displaced circumferentially from each other. The fused locations are displaced from each other through a distance equal to one-half of the length dimension of each sine wave in the single strand of wire of each ring.

In another aspect of the present invention, the fused locations are aligned in a plurality of rows that each intersects the length dimension of the elongated body at an acute angle. The rows of fused locations intersect the length dimension of the elongated body at the same acute angle such that the rows extend parallel to each other. The elongated body also has opposite front and rear sides respectively disposed distally and proximally of a clot in an occluded vessel after implanting the elongated body within a bypass graft in an anastomosis procedure. The plurality of rows of fused locations pass about the rear side of the elongated body at a height above where the plurality of rows of fused locations pass about the front side of the elongated body.

In another aspect of the present invention, an anastomosis stent includes:
- an elongated body of a tubular configuration and having a length dimension extending in an axial direction of the elongated body and a diameter dimension extending in a radial direction of the elongated body being in a transverse relationship to the axial direction of the elongated body;
- the elongated body being formed by a multiplicity of rings stacked adjacent to one another in a direction parallel to the length dimension of the elongated body, each of the rings being formed by a single strand of wire bent in a repetitive pattern of sine waves, the alternating sine wave peaks and valleys of the single strand of wire of a given ring being reversed in adjacent ones of the rings extending along opposite upper and lower sides of the given ring;
- the multiplicity of rings being fused to one another at locations on selected pairs of adjacent peaks and valleys of the sine waves in the single strand of wire of each of the rings, the fused locations being displaced circumferentially from each other so as to provide flexibility of the rings in the radial direction relative to the axial direction of the elongated body; and
- the elongated body includes
  - a main portion including a majority of the multiplicity of rings each being a continuous strand of the single wire moveable between collapsed and expanded conditions along the length dimensions of the sine waves of the continuous strands of the single wires,
  - an end portion including a minority of the multiplicity of rings at least some being continuous strands and others being discontinuous strands such that the minority of the multiplicity of rings are moveable between parallel and flared relationships to the length dimension of the elongated body, and
  - a safety mark in the form of a band of an adhesive composition encompassing the elongated body at a juncture of the main and end portions together, the safety mark used to guide accurate implanting of the elongated body.

In another aspect of the present invention, an anastomosis stent includes:
- an elongated body of a tubular configuration and having a length dimension extending in an axial direction of the elongated body and a diameter dimension extending in a radial direction of the elongated body being in a transverse relationship to the axial direction of the elongated body;
- the elongated body also having opposite front and rear sides respectively disposed distally and proximally of a clot in an occluded vessel when the elongated body is implanted in an anastomosis procedure, the elongated body being formed by a multiplicity of rings stacked adjacent to one another in a direction parallel to the length dimension of the elongated body, each of the rings being formed by a single strand of wire bent in a repetitive pattern of sine waves, each of the sine waves defining an alternating peak and valley divided by a length dimension extending orthogonal to the length dimension of the elongated body, the alternating sine wave peaks and valleys of the single strand of wire of a given ring being reversed in adjacent ones of the rings extending along opposite upper and lower sides of the given ring;
- the multiplicity of rings being fused to one another at locations on selected pairs of adjacent peaks and valleys of the rings being displaced circumferentially from each other so as to provide flexibility of the rings in the radial direction relative to the axial direction of the elongated body, the plurality of rows of fused locations extending parallel to each other and passing about the rear side of the elongated body at a height above where the plurality of rows of fused locations pass about the front side of the elongated body; and
- the elongated body includes
  - a main portion including a majority of the multiplicity of rings each being a continuous strand of the single wire moveable between collapsed and expanded conditions along the length dimensions of the sine waves of the continuous strands of the single wires, each of the rings of the main portion also moveable between symmetric and asymmetric configurations relative to the length dimension of the elongated body extending in the axial direction,
  - an end portion including a minority of the multiplicity of rings at least some being continuous strands and others being discontinuous strands such that the minority of the multiplicity of rings are moveable between parallel and flared relationships to the length dimension of the elongated body, and
  - a safety mark in the form of a band of an adhesive composition encompassing the elongated body at a juncture of the main and end portions together, the safety mark distinguishing between the opposite front and rear sides of the elongated body and used to guide accurate implanting of the elongated body.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which:

FIG. 10 presents a schematic view illustrating a next stage of the arterial anastomosis procedure in which the stent delivery instrument is withdrawn and the arterial anastomosis stent is shown in a fully expanded condition filling an end portion of the mammary artery and the flexible asymmetric end portion of the arterial anastomosis stent, that is extended into the occluded coronary artery, expanding into a flared asymmetrical condition; and.

Like reference numerals refer to like parts throughout the several views of the drawings.

DETAILED DESCRIPTION

Figure 4:
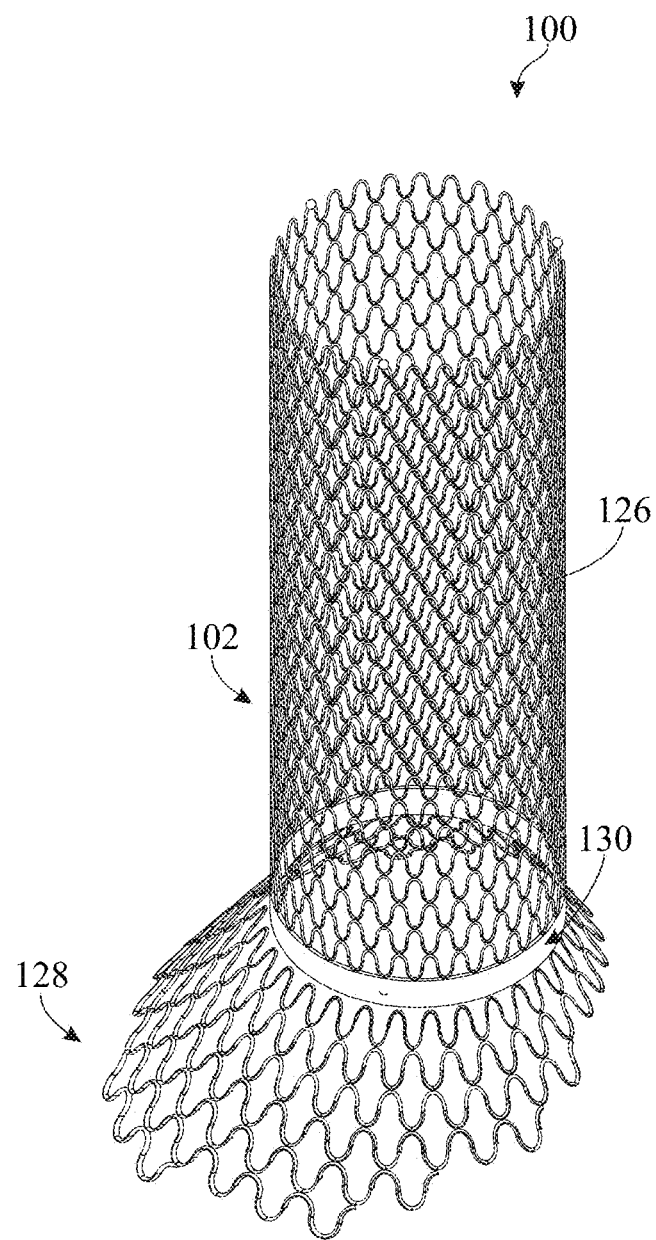
FIG. 4 presents a front isometric view on a reduced scale of the arterial anastomosis stent in the more fully self-expanded condition.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 4. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Referring now to FIGS. 1, 1A and 2-4, there is illustrated an anastomosis stent, generally designated 100, in accordance with aspects of the present invention. It is readily understood by those skilled in the art that the present embodiment of the present invention may be employed for any applicable anastomosis procedure relating to vascular and/or non-vascular tubular structures. However, Applicant has decided to focus, as an example, but not to be limited to, a stent for arterial anastomosis. Therefore, for clarity the "anastomosis stent" is herein after referred to as "an arterial anastomosis stent." The arterial anastomosis stent 100 generally comprises of an elongated body 102 of a tubular configuration. The elongated body 102 of the stent 100 has a length dimension 104 extending in an axial (longitudinal) direction of the stent 100 and a diameter dimension 106 extending in a radial direction being transverse or orthogonal to the axial direction of the stent. With respect to implanting the stent 100 in a bypass graft 204 and an occluded vessel 206 (see FIGS. 5, 10 and 11), the elongated body 102 of the stent 100 has opposite front and rear sides 107, 108 respectively disposed distally and proximally of a clot 208 located in the occluded vessel.

More particularly, the elongated body 102 of the stent 100 is formed by a multiplicity of rings 110 being stacked adjacent to one another in a direction parallel to the length dimension 104 of the elongated body. Each ring 110 is formed by a single strand of wire 112 bent into a repetitive pattern of sine waves 114. Each sine wave 114 defines an alternating peak 116 and valley 118 divided by a length dimension 120 of the sine wave extending orthogonal to the length dimension 104 of the elongated body 102. The alternating sine wave peaks 116 and valleys 118 of the sine waves 114 of the single strand of wire 112 of a given ring 110 are reversed in adjacent ones of the rings 110 extending along opposite upper and lower sides of the given ring.

The multiplicity of rings 110 of the stent elongated body 102 are fused to one another at locations 122 on selected pairs of adjacent peaks 116 and valleys 118 of the sine waves 114 of the single strand of wires 112 of the adjacent rings 110. The fused locations 122 of the selected pairs of adjacent peaks and valleys are displaced circumferentially from each other through a distance equal to one-half of the length dimension 118 of the sine wave 112 of the single strand of wire 112 of each ring 110. The fused locations 122 are thus provided in a plurality of rows 124 thereof that intersect the length dimension 104 of the elongated body 102 at an acute angle that is the same for each row. The plurality of rows 124 of the fused locations 122 extend parallel to each other and pass about the rear side 108 of the elongated body 102 at a height above where the plurality of rows of fused locations pass about the front side 106 of the elongated body so as to provide flexibility of said rings in said radial direction relative to said axial direction of said elongated body.

Figure 1:
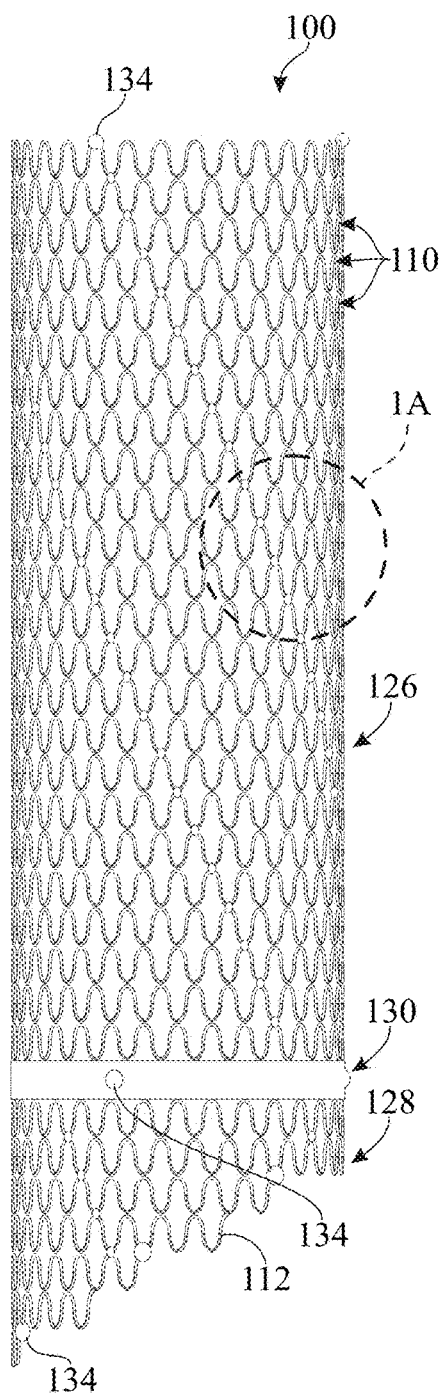
FIG. 1 presents a side elevational view of an exemplary embodiment of a longitudinally and radially flexible arterial anastomosis stent in a compressed condition according to aspects of the present invention.
Figure 2:
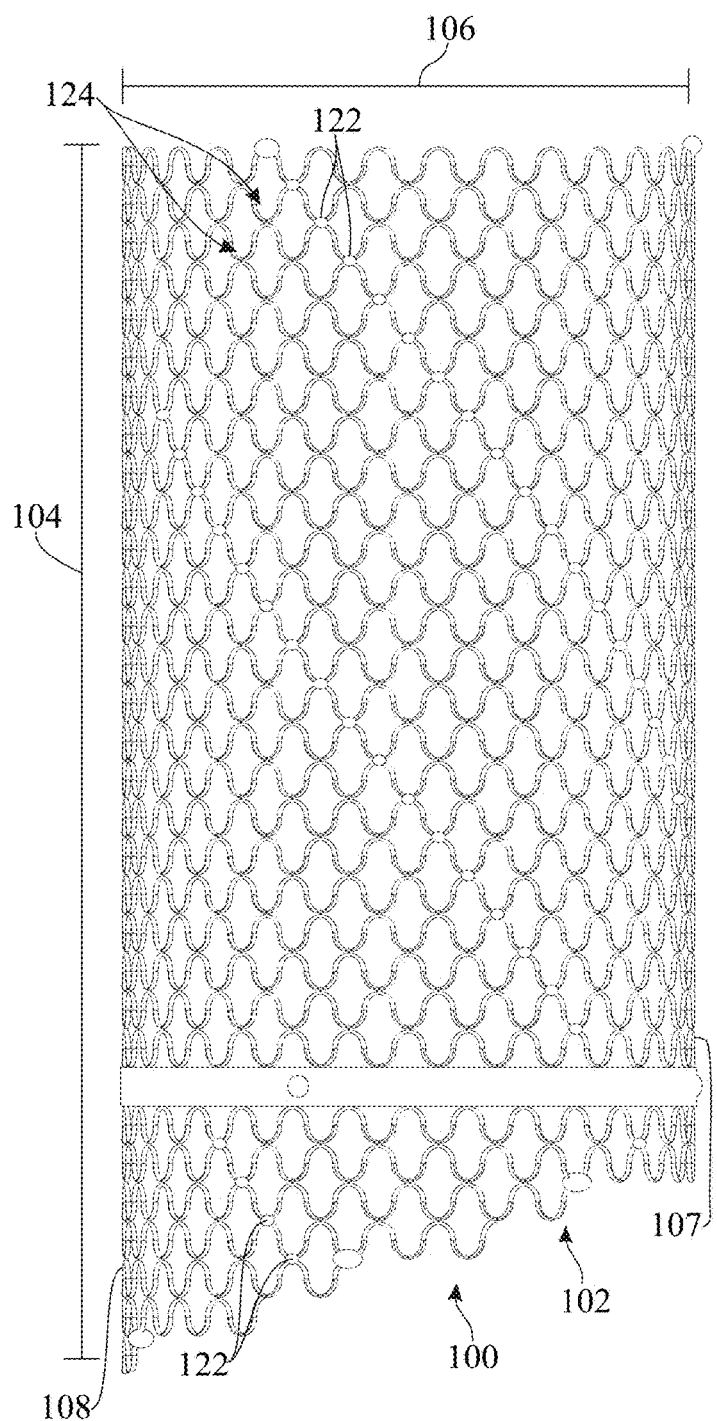
FIG. 2 presents a side elevational view of the arterial anastomosis stent originally introduced in FIG. 1, illustrated in a partially self-expanded condition.
Figure 1A:
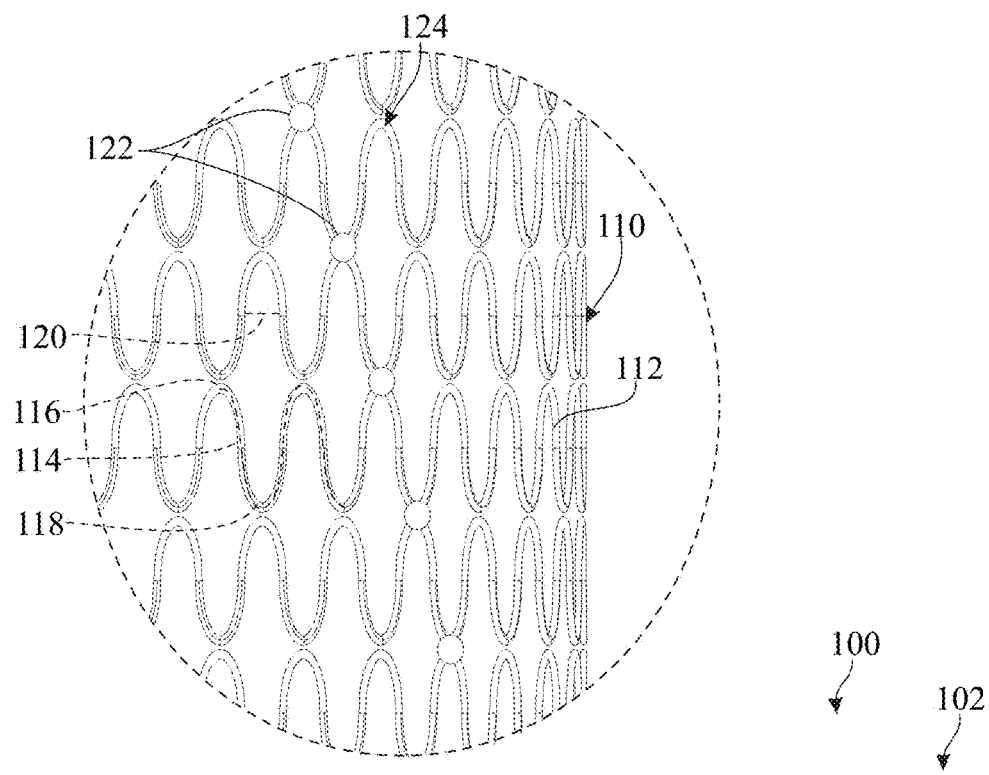
FIG. 1A presents an enlarged view of the fragmentary portion the arterial anastomosis stent enclosed by the dashed circle 1A in FIG. 1.
Figure 3:
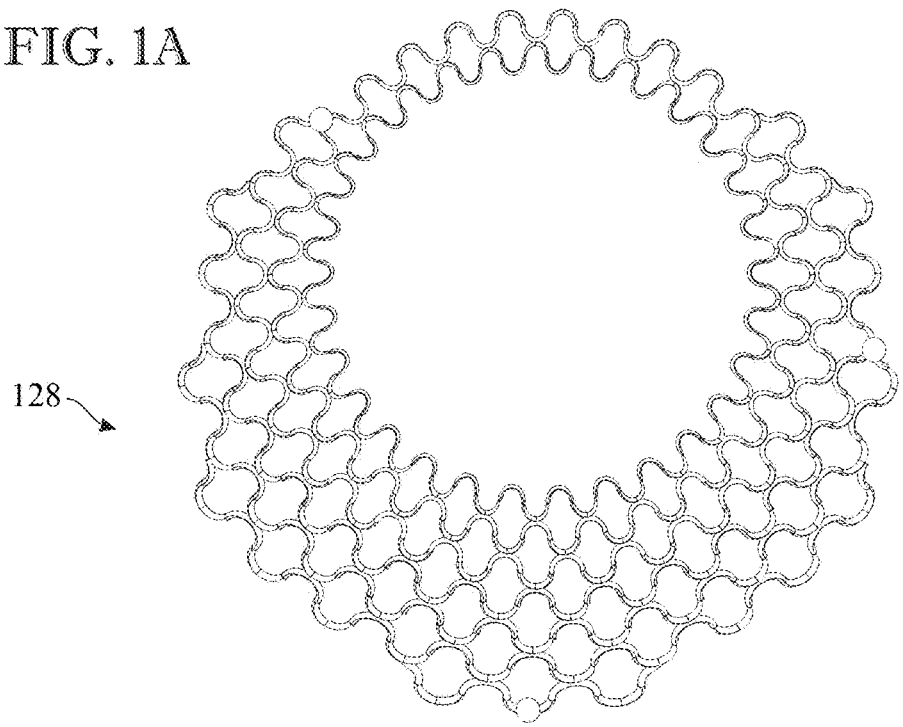
FIG. 3 presents a bottom plan view of the arterial anastomosis stent as illustrated in FIG. 4 being in a more fully self-expanded condition than shown in FIG. 2.
Figure 7:
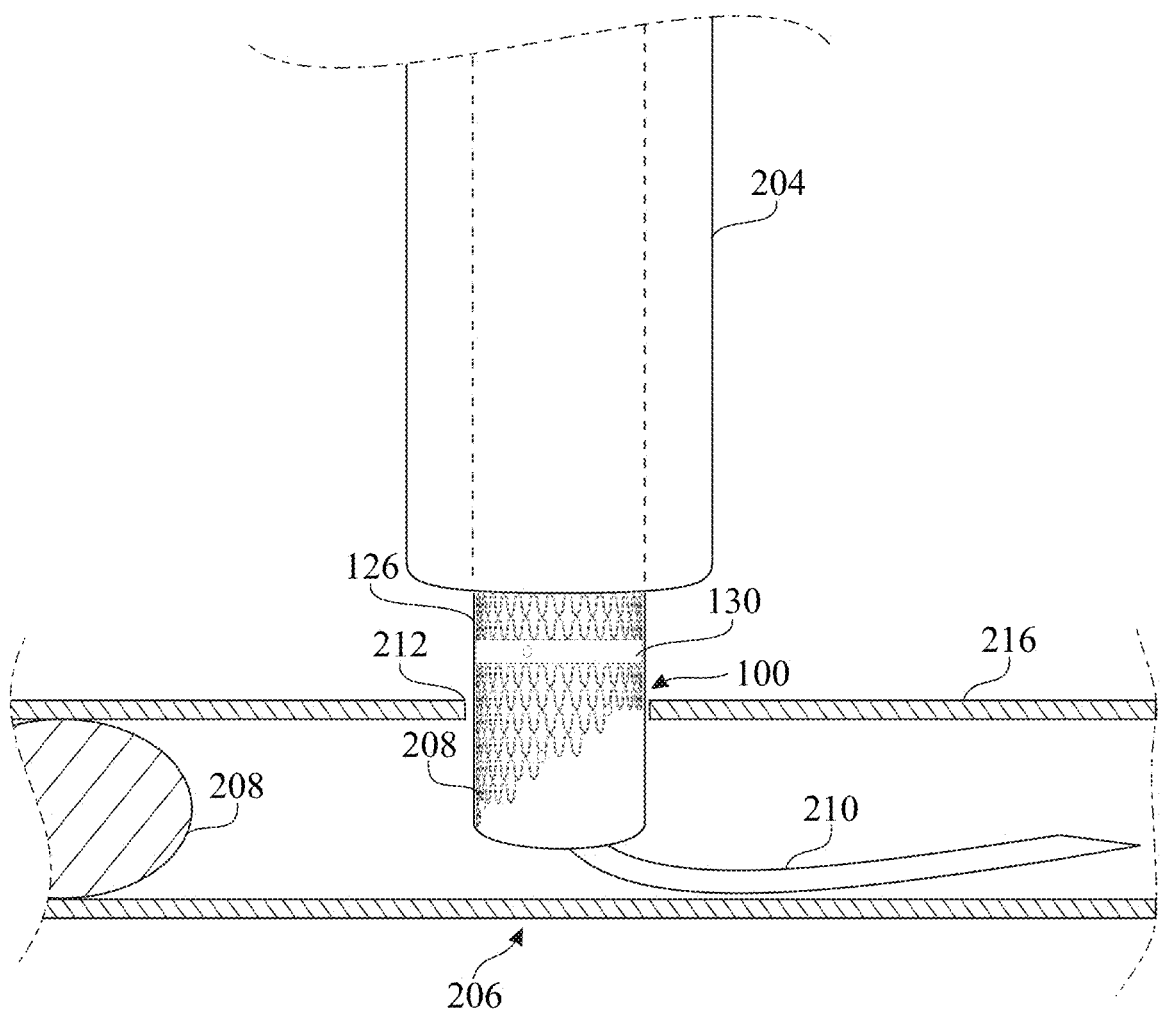
FIG. 7 presents a schematic view illustrating a next stage of the arterial anastomosis procedure in which the arterial anastomosis stent is shown emerging from the end of the mammary artery in a collapsed condition inside of the stent's delivery instrument and partially inserted through the incision in the occluded coronary artery which has expanded in size to that of the stent's delivery apparatus.
Figure 8:
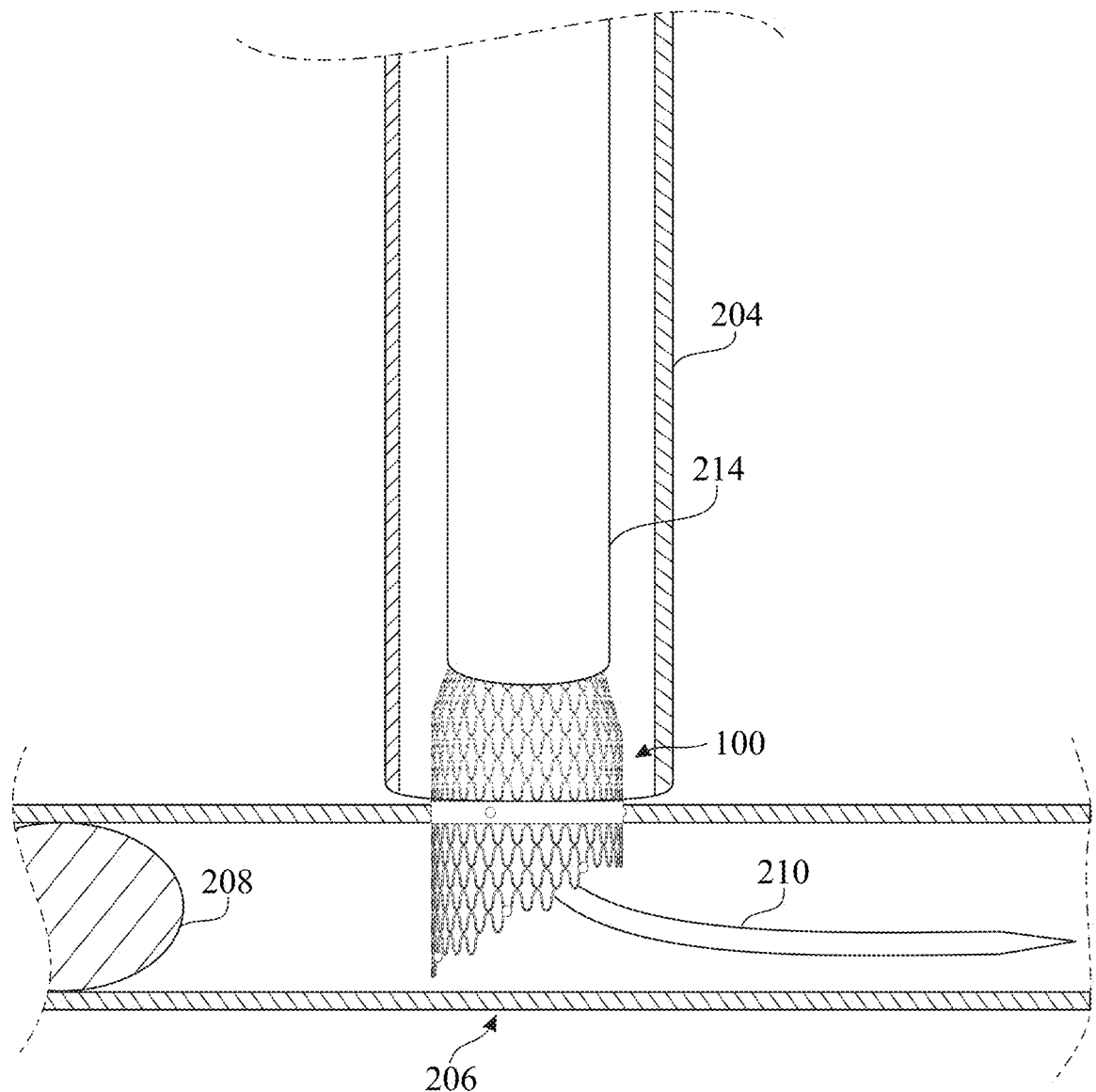
FIG. 8 presents a schematic view illustrating a next stage of the arterial anastomosis procedure in which the arterial anastomosis stent is shown emerging from the end of the mammary artery and stent delivery instrument into an expanded condition and fully inserted through the incision in the occluded coronary artery to the circumferential adhesive-based safety mark about the arterial anastomosis stent.
Figure 10:
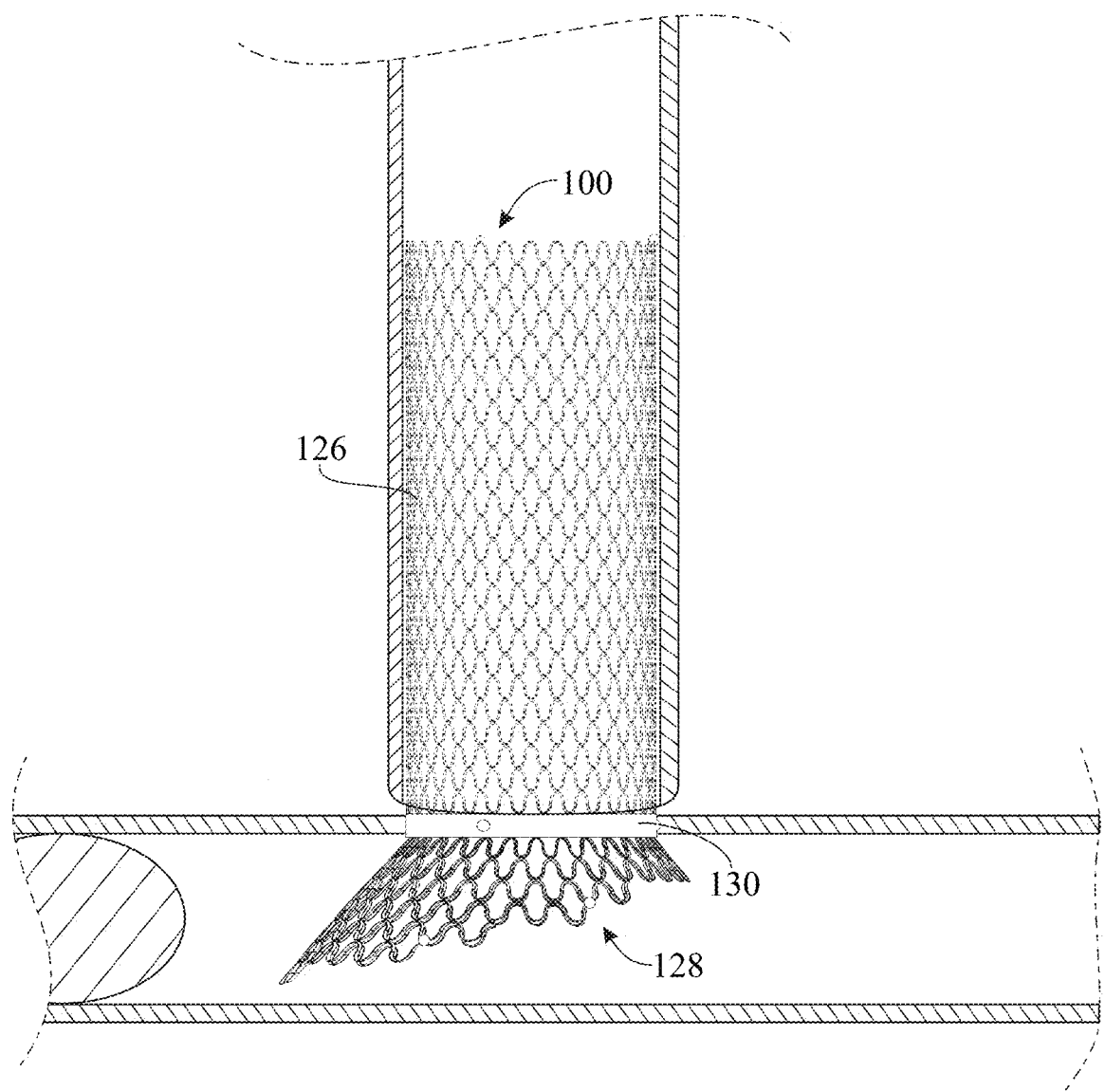
Figure 11:
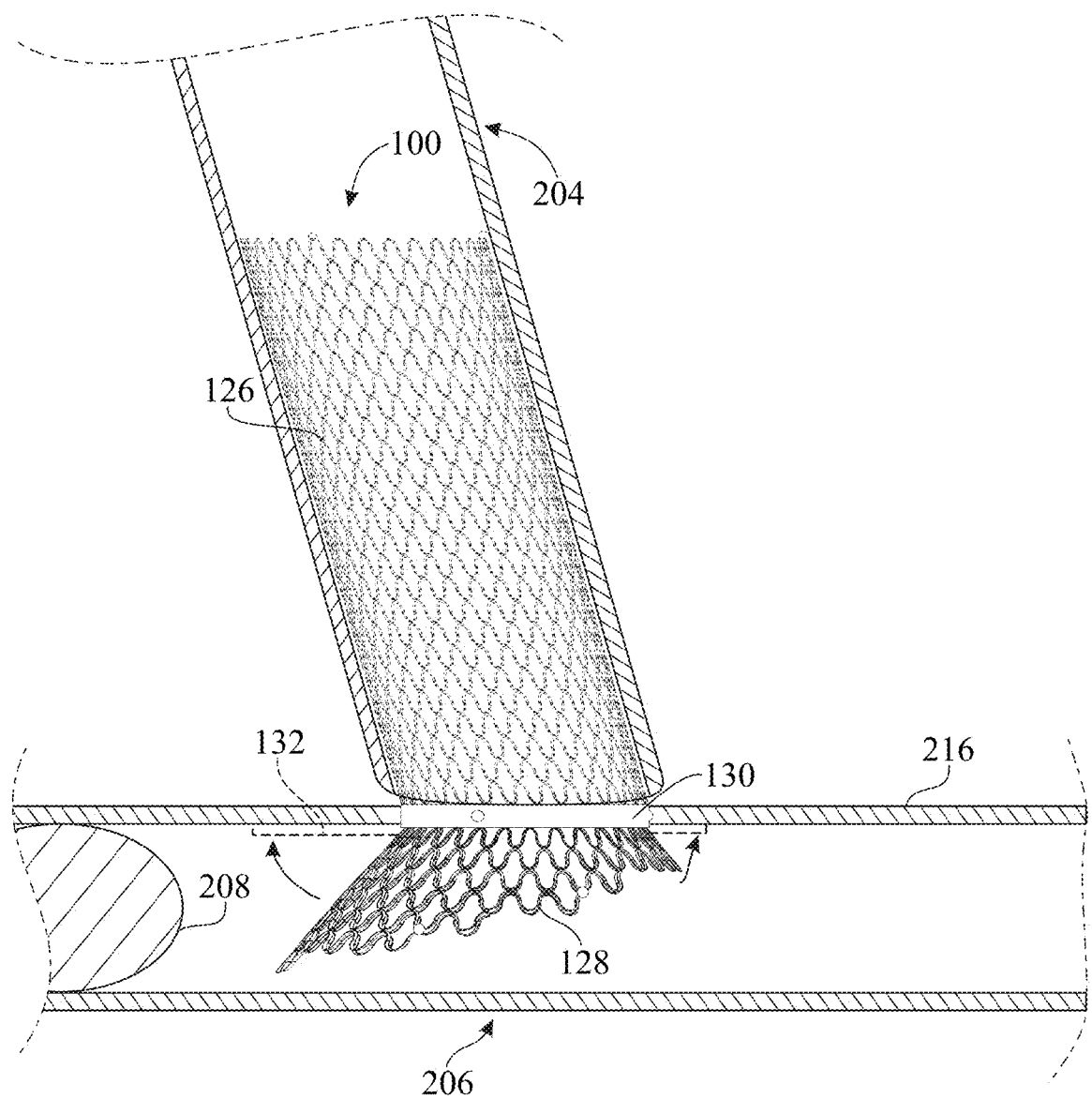
FIG. 11 presents a schematic view illustrating a final stage of the arterial anastomosis procedure in which the longitudinally and radially flexible asymmetric arterial anastomosis stent is shown in a fully expanded and in an angled position in conjunction with the mammary artery and its inserted flexible asymmetric end portion expanded from the flared asymmetrical condition of FIG. 10 to a final condition as indicated by a dashed line along the wall of the occluded coronary artery on opposite sides of the incision.

Furthermore, the elongated body 102 includes a main portion 126, an end portion 128 and a safety mark 130. The main portion 126 of the elongated body 102 incorporates a majority of the multiplicity of rings 110. Each of the rings 110 of the main portion 126 of the elongated body 102 is a continuous strand of the single wire 112. The rings 110 of the main portion 126 are radially moveable, (when self-expanding), from a collapsed condition, as seen in FIGS. 1, 7 and 8, toward an expanded condition, as seen in FIGS. 2, 4 and 9-11 along the diameter dimension 106 of the elongated body and the length dimensions 120 of the sine waves 114 of the continuous strands of the single wires 112. The normal condition (i.e. tendency) of the elongated body 102 is to be at the expanded condition. Also, the rings 110 of the main portion 126 are also moveable between a symmetric configuration (FIG. 10) and an asymmetric configuration (FIG. 11) relative to the length dimension 104 of the elongated body 102 extending in the axial direction of the stent 100. More particularly, the main portion 126 of the elongated body 102 has a tubular configuration and because of its flexible construction as described above it may shift from a symmetric rectangular diametrical sectional configuration, as seen in FIG. 10, to an asymmetric trapezoidal diametrical sectional configuration, as seen in FIG. 11, to accommodate the final position of the bypass graft 204.

The end portion 128 of the elongated body 102 incorporates a minority of the multiplicity of rings 110. Some of the rings 110 are continuous strands of single wires 112 while at least some rings are non-continuous strands of single wires. The minority of the multiplicity of rings 110 are moveable (when self-expanding) from a parallel relationship, as seen in FIGS. 1, 2, and 7-9, to a flared relationship, as seen in FIGS. 3, 4, 10 and 11, in relationship to the length dimension 104 of the elongated body 102. The safety mark 130 of the elongated body 102 is in the form of a band of a selected adhesive composition, such as a cyanoacrylate, encompassing the elongated body at the location of merger of the main and end portions 126, 128 with one another. The safety mark 130 is deployed to guide accurate implanting of the elongated body 102 of the stent 100 by indicating via fluoroscopy when the stent 100 has reached the correct position wherein the safety mark 130 is contiguous with the incision 212 in the occluded vessel 206 and the end of the bypass graft 204.

The rings 110 of the main and end portions 126, 128 of the elongated body 102 of the stent 100, by way of example but not limitation, may be formed by rolling the strands of the single wire 112 over a mandrel in a repetitive pattern of the sine wave 114 and subsequently fusing or connecting them at two or three locations 122 for each ring by use of a laser. The stent 100 may be manufactured using nitinol alloy, and may be supplied in different lengths of about 6-8 mm and diameters of about 2-4 mm. Once manufactured, the stent 100 may be coated with an antibacterial and/or immunosuppressant solution, by way of example, but not be limited to, Zotarolimus and BioLinx® polymer. It will be apparent to those skilled in the art that the type of antibacterial and/or polymer used to coat the stent 100 may vary depending on the patient's needs. For example, an article describing the advantages and disadvantages of applying non-biodegradable polymers to the stent 100 is provided at http://circinterventions.ahajournals.org/content/9/6/e002943, the entire contents of which are incorporated-by-reference herein. Once the stent 100 is coated with a polymer and/or antibacterial solution, a coating of polytetrafluoroethylene (PTFE) is applied to reduce the percentage of thrombosis (i.e. the formation of blood clots inside of the blood vessel). The main and end portions 126, 128 may include deposits of tantalum in the form of visual indicators (e.g. nodes) 134 at opposite ends of the elongated body 102 and at the safety mark 130 thereof to enable the physician to identify the correct orientation of the stent 100 via fluoroscopy. The main portion 126 of the elongated body 102 of the stent 100 resembles a crown of a hat, whereas the end portion 128 of the elongated body of the stent resembles a brim or wings of the hat. As the crown, which is cylindrical, expands in the radial direction, the wings open.

Figure 5:
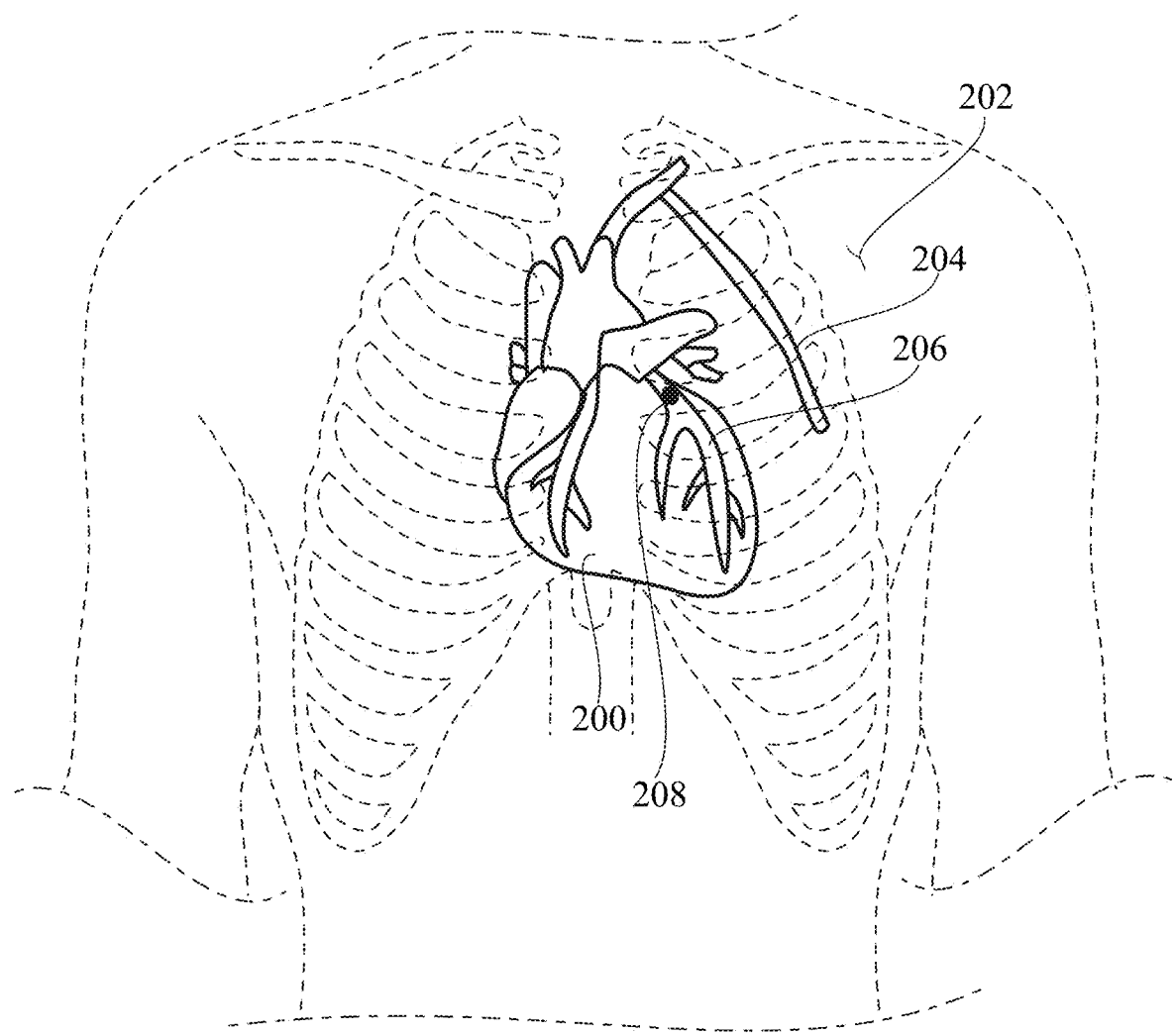
FIG. 5 presents a front schematic view of a heart in the chest of a human body showing a mammary artery selected to be joined to an occluded coronary artery of the heart downstream of a clot in the coronary artery to bypass the clot and restore oxygen and blood flow.

Turning now to FIG. 5, there is illustrated a heart 200 in the chest 202 of a human body showing the bypass graft 204, such as a mammary artery, selected to be joined to the occluded vessel 206, such as a coronary artery, of the heart downstream of the clot 208 in the coronary artery in order to bypass the clot and restore blood flow. In FIGS. 6-11 there is shown a succession of stages for carrying out an arterial anastomosis procedure to implant the longitudinally and laterally flexible arterial anastomosis stent 100 of FIGS. 1-4 so as to extend from the mammary artery 204 into the occluded coronary artery 206 to bypass the clot 208 therein.

Figure 6:
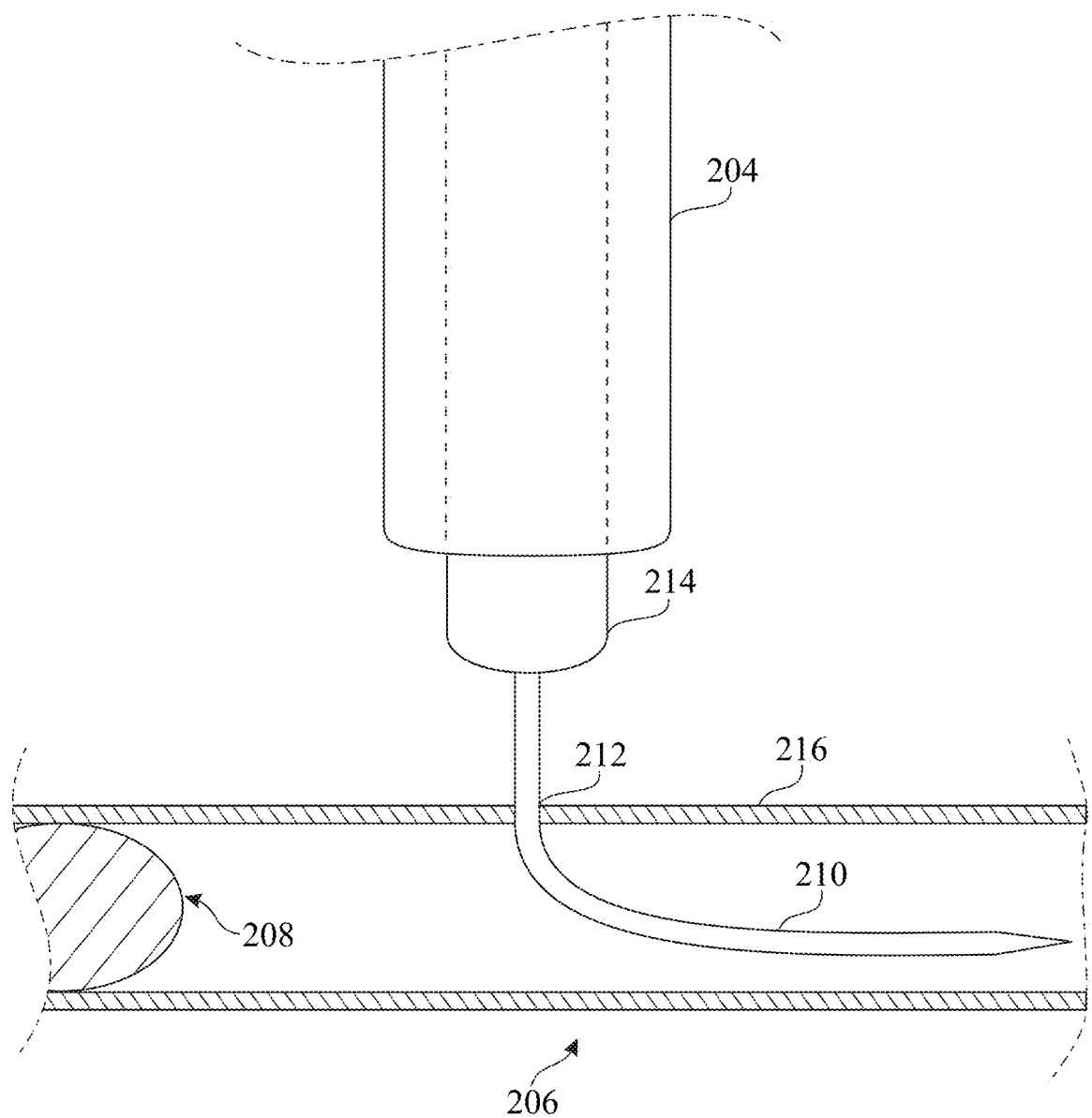
FIG. 6 presents a schematic view of the occluded coronary artery having a clot therein blocking blood flow and illustrating, in an early stage of an arterial anastomosis procedure for implanting the arterial anastomosis stent, a leading portion of a guide wire extending from a leading end of a stent delivery instrument extending from a mammary artery and spaced from an incision made in the occluded coronary artery downstream of the clot and through which the leading portion of the guide wire is inserted so that it extends downstream in a direction away from the clot.

More particularly, in FIG. 6 a portion of the coronary artery 206 with a clot 208 therein blocking blood flow is shown. Also shown is an early stage of an arterial anastomosis procedure to implant the stent (not currently shown). A leading portion of a guide wire 210 extends from a leading end of the stent held at an end of a stent delivery apparatus 214, for example, but not to be limited to, a release system by Jaguar® or Boston Scientific® along with a catheter (also not shown). The instrument extends within the mammary artery 204 to an end thereof spaced from the incision 212 made in the coronary artery 206 downstream of the clot 208 and through which the leading portion of the guide wire 210 is inserted so that it extends downstream in a direction away from the clot.

As is shown in FIGS. 7-11, the stages of the arterial anastomosis procedure are generally shown. In a general representation of the procedural implantation of the arterial stent 100, as is shown in FIG. 7, the stent appears in a collapsed condition emerging from the end of the mammary artery 204 and the distal end of the stent delivery apparatus 214. The stent 100 is partially inserted through the incision 212 in the coronary artery 206 which has been shown expanded in size to that of the collapsed stent 100. Turning now to FIG. 8, the arterial anastomosis stent 100 is generally shown emerging from the end of the mammary artery 204 and the stent delivery apparatus 214 into a self-expanding condition. The stent 100 is full inserted through the incision 212 in the coronary artery 206 up to the safety mark 130 about the stent 100.

Figure 9:
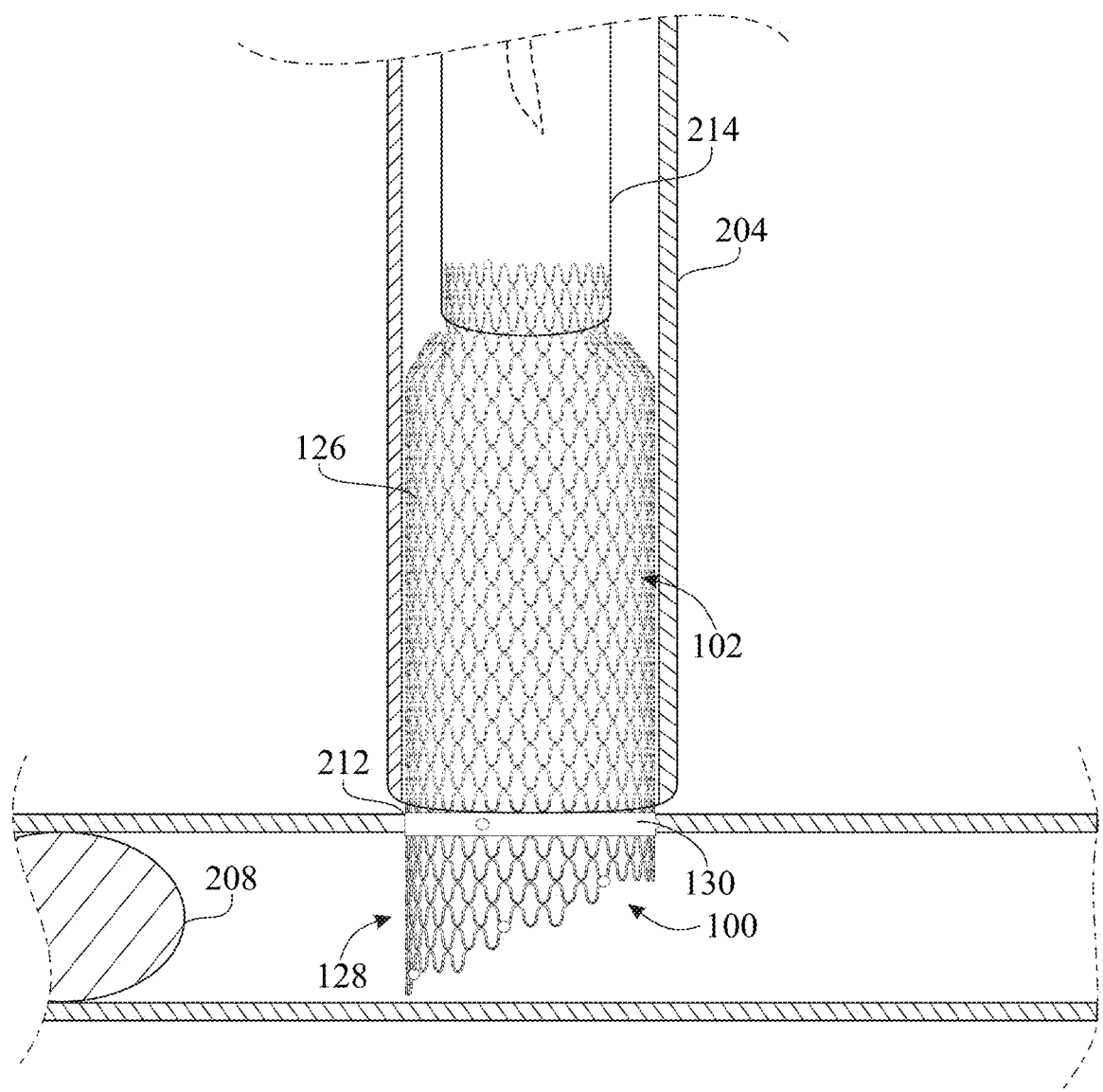
FIG. 9 presents a schematic view illustrating a next stage of the arterial anastomosis procedure in which the anastomosis stent is shown almost fully emerged from the end of the stent delivery instrument into its expanded condition with a flexible asymmetric end portion of the arterial anastomosis stent being fully inserted through the incision in the occluded coronary artery.

Once the stent 100 has been fully inserted through the incision 212 and the coronary artery 206 up to the safety mark 130, the stent 100 is considered to be in the ideal position for anastomosis and the stent delivery apparatus may be fully retracted, as is shown in FIG. 9. Referring to FIG. 10, now that the stent delivery apparatus 214 has been withdrawn the arterial anastomosis stent 100 is in a fully expanded condition filing the end portion of the mammary artery 204, and an asymmetric end portion 128 of the arterial stent 100 is extended into the coronary artery 206, expanding to a flared asymmetric condition.

As is shown in FIG. 11, to complete the anastomosis process the arterial stent 100 which is now in a fully expanded condition in the mammary artery 204 is angled, within an approximate range of about 30 to about 60 degrees, with respect to coronary artery 206. The arterial stent's 100 end portion 128 that has expanded from the flared asymmetric condition shown in FIG. 10 is now in a final condition indicated by a dashed line 132 along the (upper) wall 216 of the coronary artery on opposite sides of the incision 212. The stent's end portion 128 asymmetrical condition along with the angled position of the stent 100 and mammary artery 204 is paramount for the restoration of positive blood and oxygen flow opposite the blood clot 208, thus reducing the amount of backflow in the direction of the clot 208 (i.e. the angle of the mammary artery and asymmetrical condition of the end portion of the stent provide positive blood flow into the heart and away from the clot).

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A anastomosis stent, comprising:
an elongated body of a tubular configuration and having a length dimension extending in an axial direction of said elongated body and a diameter dimension extending in a radial direction of said elongated body being in a transverse relationship to said axial direction of said elongated body;
said elongated body being formed by a multiplicity of rings stacked adjacent to one another in a direction parallel to said length dimension of said elongated body, each of said rings being formed by a single strand of wire bent in a repetitive pattern of sine waves, said alternating peaks and valleys of said sine waves of said single strand of wire of a given ring being reversed in adjacent ones of said rings extending along opposite upper and lower sides of said given ring;
said multiplicity of rings being fused to one another at locations on selected pairs of adjacent peaks and valleys of said sine waves in said single strand of wire of each of said rings, said fused locations being displaced circumferentially from each other so as to provide flexibility of said rings in said radial direction relative to said axial direction of said elongated body; and
said elongated body comprising
a main portion comprising a majority of said multiplicity of rings each being a continuous strand of said single wire moveable between collapsed and expanded conditions along said length dimensions of said sine waves of said continuous strands of said single wires,
an end portion comprising a minority of said multiplicity of rings at least some being continuous strands and others being discontinuous strands such that said minority of said multiplicity of rings are moveable between parallel and flared relationships to said length dimension of said elongated body, and
a safety mark in the form of a band of an adhesive composition encompassing said elongated body at a juncture of said main and end portions together, said safety mark being used to guide accurate implanting of said elongated body.

2. The anastomosis stent of claim 1 wherein said single wire of each of said rings is made of a nitinol alloy that is coated with an antibacterial and polymeric substance.

3. The anastomosis stent of claim 1 wherein said alternating peak and valley of each of said sine waves in said single strand of wire of a given ring is divided by a length dimension extending orthogonal to said length dimension of said elongated body.

4. The anastomosis stent of claim 3 wherein said fused locations are displaced from each other through a distance equal to one-half of said length dimension of each of said sine waves in said single strand of wire of said each ring.

5. The anastomosis stent of claim 1 wherein each of said rows of fused locations intersects said length dimension of said elongated body at an acute angle.

6. The anastomosis stent of claim 1 wherein said elongated body also has opposite front and rear sides respectively disposed distally and proximally of a clot in an occluded vessel when said elongated body is implanted in an anastomosis procedure, said safety mark distinguishing between said opposite front and rear sides of said elongated body to guide accurate implanting of said elongated body.

7. An anastomosis stent, comprising:
an elongated body of a tubular configuration and having a length dimension extending in an axial direction of said elongated body and a diameter dimension extending in a radial direction of said elongated body being in a transverse relationship to the said direction of said elongated body;
said elongated body also having opposite front and rear sides respectively disposed distally and proximally of a clot in an occluded vessel when said elongated body is implanted in an anastomosis procedure;
said elongated body being formed by a multiplicity of rings stacked adjacent to one another in a direction parallel to said length dimension of said elongated body, each of said rings being formed by a single strand of wire bent in a repetitive pattern of sine waves, each of said sine waves defining an alternating peak and valley divided by a length dimension extending orthogonal to said length dimension of said elongated body, said alternating sine wave peaks and valleys of said single strand of wire of a given ring being reversed in adjacent ones of said rings extending along opposite upper and lower sides of said given ring;
said multiplicity of rings being fused to one another at locations on selected pairs of adjacent peaks and valleys of said sine waves of said single wire of each of said rings, said fused locations being displaced circumferentially from each other, said plurality of rows of said fused locations extending parallel to each other and passing about said rear side of said elongated body at a height above where said plurality of rows of said fused locations pass about said front side of said elongated body so as to provide flexibility of said rings in said radial direction relative to said axial direction of said elongated body; and
said elongated body comprising
a main portion comprising a majority of said multiplicity of rings each being a continuous strand of said single wire moveable between collapsed and expanded conditions along said length dimensions of said sine waves of said continuous strands of said single wires, each of said rings of said main portion also moveable between a symmetric configuration and an asymmetric configuration relative to said length dimension of said elongated body extending in said axial direction,
an end portion comprising a minority of said multiplicity of rings at least some being continuous strands and others being discontinuous strands such that said minority of said multiplicity of rings are moveable between parallel and flared relationships to said length dimension of said elongated body, and a safety mark in the form of a band of an adhesive composition encompassing said elongated body at a juncture of said main and end portions together, said safety mark distinguishing between said opposite front and rear sides of said elongated body and used to guide accurate implanting of said elongated body.

8. The anastomosis stent of claim 7 wherein the single wire of each of the rings is made of a nitinol alloy that is coated with an antibacterial and polymeric substance.

9. The anastomosis stent of claim 7 wherein each of said sine waves defines an alternating peak and valley divided by a length dimension extending orthogonal to said length dimension of said elongated body.

10. The anastomosis stent of claim 7 wherein said fused locations are in a plurality of rows that intersect said length dimension of said elongated body at an acute angle being the same for each row.

11. The anastomosis stent of claim 7 wherein said plurality of rows of fused locations pass about said rear side of said elongated body at a height above where said plurality of rows of fused locations pass about said front side of said elongated body.

\* \* \* \* \*